(12) United States Patent
Ahlgren et al.

(10) Patent No.: US 11,946,090 B2
(45) Date of Patent: Apr. 2, 2024

(54) SYSTEM AND METHOD FOR TREATING BIOMASS MATERIAL

(71) Applicant: VALMET AB, Sundsvall (SE)

(72) Inventors: Örjan Ahlgren, Sundsvall (SE); Johan Carlsson, Alnö (SE); Anders Löfström, Alnö (SE); Patrik Pettersson, Alnö (SE)

(73) Assignee: VALMET AB, Sundsvall (SE)

( * ) Notice: Subject to any disclaimer, the term of this patent is extended or adjusted under 35 U.S.C. 154(b) by 274 days.

(21) Appl. No.: 17/267,590

(22) PCT Filed: May 29, 2019

(86) PCT No.: PCT/SE2019/050500
§ 371 (c)(1),
(2) Date: Feb. 10, 2021

(87) PCT Pub. No.: WO2020/040677
PCT Pub. Date: Feb. 27, 2020

(65) Prior Publication Data
US 2021/0310029 A1    Oct. 7, 2021

(30) Foreign Application Priority Data
Aug. 24, 2018  (SE) .................................. 1851014-9

(51) Int. Cl.
*C12P 7/10* (2006.01)

(52) U.S. Cl.
CPC ............. *C12P 7/10* (2013.01); *C12P 2201/00* (2013.01)

(58) Field of Classification Search
None
See application file for complete search history.

(56) References Cited

U.S. PATENT DOCUMENTS

| | | |
|---|---|---|
| 2009/0061495 A1 | 3/2009 | Beatty et al. |
| 2011/0281298 A1 | 11/2011 | Rawls et al. |
| 2012/0211183 A1 | 8/2012 | Leavitt et al. |
| 2013/0029406 A1 | 1/2013 | Dottori et al. |
| 2014/0288298 A1 | 9/2014 | Nakagame et al. |
| 2016/0076198 A1 | 3/2016 | Christensen et al. |
| 2021/0310029 A1* | 10/2021 | Ahlgren ................... C12P 7/10 |

FOREIGN PATENT DOCUMENTS

| | | |
|---|---|---|
| EP | 3 333 310 A1 | 6/2018 |
| EP | 3399095 A1 | 11/2018 |
| JP | 2012-000022 A | 1/2012 |
| WO | WO 2004/005608 A1 | 1/2004 |
| WO | WO 2010/022511 A1 | 3/2010 |
| WO | WO 2013/000088 A1 | 1/2013 |
| WO | WO 2013/126007 A1 | 8/2013 |
| WO | WO-2013/186184 A1 | 12/2013 |
| WO | WO 2015/199604 A1 | 12/2015 |
| WO | WO-2017/088061 A1 | 6/2017 |
| WO | WO 2018/202673 A1 | 11/2018 |

OTHER PUBLICATIONS

Ye et al. (Algal Research, vol. 31 (2018), pp. 421-429).*
Extended European Search Report, EP Application No. 19852122.1, dated May 18, 2022, 5 pages.
Swedish Search Report, Application No. 1851014-9, dated Mar. 11, 2019, 3 pages.
Carrasco et al., "Kinetic study of dilute-acid prehydrolysis of xylan-containing biomass*," Wood Science and Technology, 1992, vol. 26 (pp. 189-207).
Devi et al., "Lignocellulosic Biomass Valorization for Bioethanol Production: a Circular Bioeconomy Approach," BioEnergy Research, 2022, vol. 15 (pp. 1820-1841).
Office Action in European Patent Appl. No. 19852122.1, dated Jul. 4, 2023.
Science Direct, "Kraft Process—an overview," URL: https://www.sciencedirect.com/topics/engineering/kraft-process, retrieved from internet Jul. 2, 2023.

* cited by examiner

*Primary Examiner* — Hope A Robinson
(74) *Attorney, Agent, or Firm* — Foley & Lardner LLP

(57) ABSTRACT

According to the present invention, there is provided a treatment process system for biomass material and methods for such system. The system comprises a first dewatering stage arranged to receive biomass material, to remove liquid from the biomass material, and to feed the biomass material forward in the process. Further, the system includes a water treatment stage arranged to collect the removed liquid and an addition stage located downstream said dewatering stage and operatively coupled to the first dewatering stage. The addition stage is arranged to receive the de-watered biomass material, wherein the addition stage includes inlets for adding acid containing solution into the addition stage. A reactor stage arranged to receive the biomass material treated in the addition stage and to perform a pre-hydrolysis process to the biomass material. A filtrate feeding arrangement is arranged to feed liquid from the filtrate tank to the reactor stage.

24 Claims, 12 Drawing Sheets

US 11,946,090 B2

SYSTEM AND METHOD FOR TREATING BIOMASS MATERIAL

CROSS-REFERENCE TO RELATED APPLICATION

This is a national stage application of PCT Application No. PCT/SE2019/050500, filed on May 29, 2019, which claims priority to Swedish Application No. 1851014-9, filed on Aug. 24, 2018.

TECHNICAL FIELD

The present invention relates to feeding arrangements and systems for hydrolysis and pre-hydrolysis processes for production of biofuels such as ethanol using, e.g. biodegradable waste, or ligno-cellulosic biomass material including wood waste, e.g. saw dust, or plant material including annual plants.

BACKGROUND OF THE INVENTION

The oil resources in the world are diminishing at the same time as the demand for energy increases. This increasing demand for energy cannot be meet by fossil sources since the global emissions of greenhouse gases, such as $CO_2$, needs to be reduced. This is particularly important within the transportation sector and the development of efficient methods for producing biofuels, both in terms of usage of resources and economy, are therefore critical. Ethanol has been an alternative for gasoline for many years but has now become an increasingly important biofuel as source for motor fuel and fuel additive. Ethanol can be produced from biodegradable waste, e.g. food waste, grain-based feed stocks, e.g. corn, wheat, or soybeans, from sugar, e.g. from sugar beets, from biomass, ligno-cellulosic biomass material such as wood, or plant material including annual plants.

In current processes for producing biofuel, such as ethanol, the raw material is fed into a pre-hydrolysis reactor. The raw material can also be pre-steamed or pre-impregnated before being fed into the pre-hydrolysis reactor or other chemical reactor. Usually an acidifying chemical, e.g. $H_2SO_4$, is added in a process stage up-stream the reactor, for example in an impregnation stage, in a soaking stage or in a mixer screw by spraying. The acidified material is then fed into the reactor using a feeding device, e.g. a plug screw feeder, and a major part of the liquid in the material is removed as filtrate. The filtrate is then recirculated in the process and used to impregnate or to spray raw material fed into the process together with acidifying chemicals. When using raw material with a high moisture content, the amount of filtrate that is removed in the plug screw is higher than the amount of filtrate that is needed to acidify the raw material. Therefore, the remaining surplus filtrate is fed into the pre-hydrolysis reactor, or other chemical reactor in the process. However, this surplus filtrate contains acidifying chemicals which results in inter alia corrosion in the reactor and negative effects in the process itself within the reactor if filtrate containing acidifying chemical is sprayed on the surface of the raw material. For example, it may result in a faster reaction at the surface of the material. In addition, it is also difficult to handle the high amount of surplus filtrate containing acidifying chemicals in a waste water plant.

Thus, there is a need for improved processes and systems for treating biomass in pre-hydrolysis systems for biofuel production.

SUMMARY OF THE INVENTION

An object of the present invention is to provide improved processes and systems for treating biomass in pre-hydrolysis systems for biofuel production.

Another object of the present invention is to provide a more efficient handling of liquid and water in processes and systems for treating biomass in pre-hydrolysis systems for biofuel production.

A further object of the present invention is to provide processes and systems for treating biomass in pre-hydrolysis systems for biofuel production where the wear such as corrosion can be significantly reduced in essential parts of the system such as the pre-hydrolysis reactor.

Yet another object of the system is to provide processes and systems for treating biomass in pre-hydrolysis systems for biofuel production that are capable of using raw material with a high degree of moisture without affecting the balance of the system and with an efficient water usage.

These and other objects are met by the present invention as defined by the claims and embodiments described herein.

According to an aspect of the present invention, there is provided a treatment process system for biomass material comprising a first dewatering stage arranged to receive biomass material, to remove liquid from the biomass material, and to feed the biomass material forward in the process. Further, the system includes a water treatment state arranged or configured to collect and perform a water treatment process on the removed liquid from the first dewatering stage. In embodiments of the present invention, the water treatment stage includes a water-purifying unit, which can be, for example, a biological purifying unit or a chemical purifying unit, a unit for changing pH of the water by adding an acid or a base.

An addition stage is located downstream the dewatering stage and is operatively coupled to the first dewatering stage. The addition stage is arranged to receive the de-watered biomass material, wherein the addition stage includes inlets for adding acid containing solution into the addition stage. A reactor stage is arranged to receive the biomass material treated in the addition stage and to perform a pre-hydrolysis process to the biomass material.

According to a further aspect of the present invention, there is provided a treatment process system for biomass material comprising a first dewatering stage arranged to receive biomass material, to remove liquid from the biomass material, and to feed the biomass material forward in the process. Further, the system includes a first filtrate tank operatively coupled to the first dewatering stage and is arranged to collect the liquid removed in the first dewatering stage. An addition stage is located downstream the dewatering stage and is operatively coupled to the first dewatering stage. The addition stage is arranged to receive the de-watered biomass material, wherein the addition stage includes inlets for adding acid containing solution into the addition stage. A reactor stage arranged to receive the biomass material treated in the addition stage and to perform a pre-hydrolysis process to the biomass material. A filtrate feeding arrangement is operatively coupled to the first filtrate tank and is arranged to feed liquid from the filtrate tank to the reactor stage. Thus, the liquid or water removed from the biomass in the first dewatering stage is re-cycled in the process downstream the stage where acid is added. As understood from the present application, the liquid or water can be passed through a filtering or screening stage before being fed to the reactor, where it can be fed to a discharge part including a discharging screw, to cleaning nozzles arranged into the reactor or an inlet part of the reactor. The filtrate may also, or instead, be fed upstream in the process to the dewatering stage, the silo, or a washing stage upstream the silo.

According to another aspect of the present invention, there is provided a method or process for treating biomass material comprising the steps of: removing liquid from the biomass material in a first de-watering stage for water treatment; adding an acid containing solution to the biomass material; and performing a pre-hydrolysis process in a reactor stage on the biomass material.

According to another aspect of the present invention, there is provided a method or process for treating biomass material comprising the steps of: removing liquid from the biomass material in a first de-watering stage; collecting the removed liquid from the first de-watering stage; adding an acid containing solution to the biomass material; performing a pre-hydrolysis process in a reactor stage on the biomass material; and recycling the collected liquid from first de-watering stage to the reactor stage.

The present invention is based on the insight that by performing a dewatering process up-stream the addition stage where chemicals, such as e.g. sulfuric acid ($H_2SO_4$), are added to the biomass material, surplus filtrate of the biomass material can be collected and cleaned or treated in a water treatment stage. By arranged a dewatering stage upstream the stage where chemical are added, the water treatment is significantly simplified since equipment for cleaning or removing acids or chemicals from the liquid or water is not needed. According to aspect of the invention, the surplus filtrate that is removed in the dewatering stage is re-cycled into the process downstream the acid-addition stage, for example, in the reactor stage, which hence is possible without any special concerns required when the filtrate contains acidifying chemicals.

For example, the filtrate can be collected and fed directly into the reactor stage or it can be sent to waste water treatment without any pre-treatment stage since it does not contain any acidifying chemicals.

In other words, the present invention is based on the idea of adding a first de-watering step or stage before the addition of chemical, such as acidifying liquids, to thereby enabling recovery of filtrate without any added chemicals. This makes it possible to flexible use of the surplus filtrate in the process, for example, in the reactor without any risk for corrosion inside the reactor vessel. Another advantage is that the amount of process water used in the system can be reduced since the recycling of filtrate is significantly improved by the present invention.

In embodiments of the present invention, the he filtrate feeding arrangement is arranged to feed liquid from the filtrate tank to cleaning nozzles of the reactor stage.

In other embodiments of the present invention, the filtrate feeding arrangement is arranged to feed liquid from the filtrate tank to a discharge unit of the reactor stage.

According to further embodiments, the filtrate feeding arrangement is arranged to feed liquid from the filtrate tank to an inlet part of the reactor stage.

In yet other embodiments of the present invention, the addition stage comprises an impregnator, or a soaking unit, or a mixer screw, or a PREX impregnation system (a Valmet product).

In embodiments, a second dewatering stage is arranged downstream the addition stage and operatively coupled to the addition stage. The second dewatering stage is arranged to receive biomass material, to remove liquid from the biomass material, and to feed the biomass material forward in the process.

According to embodiments of the present invention, a second filtrate tank is arranged to collect removed liquid from the second dewatering stage and a re-circulation arrangement is arranged to feed liquid from the second filtrate tank to the addition stage.

In embodiments of the present invention, the inlets for adding acid containing solution are controlled to add acid containing solution to the biomass material such that an acid content is a range of 0-10% weight/weight of the biomass material, or in a range of 0.001-10% weight/weight of the biomass material. In embodiments, sulfuric acid ($H_2SO_4$) is added to the biomass material.

In further embodiments of the present invention, the first and second de-watering stages and addition stage are arranged to operate at atmospheric pressure.

In embodiments of the present invention, the reactor stage is arranged to operate at a pressure in a range of 5-25 bar and/or a temperature in a range of 150° C.-230° C.

According to embodiments of the present invention, a pre-steaming stage is arranged up-stream said first de-watering stage, said pre-steaming stage being arranged to perform a pre-steaming process on said biomass material.

In embodiments of the present invention, a recovery and refining stage is coupled to the first filtrate tank and is arranged to perform a refining process on the filtrate to recover selected compounds from the filtrate.

In other embodiments of the present invention, a recovery and refining stage is coupled to the first filtrate tank and is arranged to perform a refining process on the filtrate to recover selected compounds from the filtrate.

In the context of the present invention, the term "plug screw feeder" relates to a feeder comprising a screw or similar rotating means and which is capable of feeding or transporting lignocellulosic material through the feeder at increased or maintained density of the material and that creates an essentially gas- and fluid-tight plug of the lignocellulosic material towards the end of the feeder. For example, according to an embodiment of such a plug screw feeder, a cross-sectional area of the circular housing of the feeder and the screw diameter decreases in the feeding direction thereby so as to create a decreasing space between the screw and the housing and thus resulting in an essentially gas- and fluid-tight plug of the lignocellulosic material towards the end of the feeder. According to another embodiment of a plug screw feeder, the cross-sectional area of the circular housing of the feeder is constant while and the screw diameter and screw axis increases in the feeding direction thereby creating a decreasing space between the screw and the housing and thus resulting in an essentially gas- and fluid-tight plug of the lignocellulosic material towards the end of the feeder. As the skilled person realizes, there are other embodiments of feeders that achieves this purpose and thus are included within the definition of the term "plug screw feeder". Further, a force-feeding screw that may be used in the present invention is described in, for example, WO 2013126007.

Further advantageous embodiments of the device according to the present invention and further advantages with the present invention emerge from the detailed description of embodiments.

BRIEF DESCRIPTION OF THE DRAWINGS

The present invention will now be described, for exemplary purposes, in more detail by way of embodiments and with reference to the enclosed drawings, in which.

DETAILED DESCRIPTION OF PREFERRED EMBODIMENTS

Figure 1:
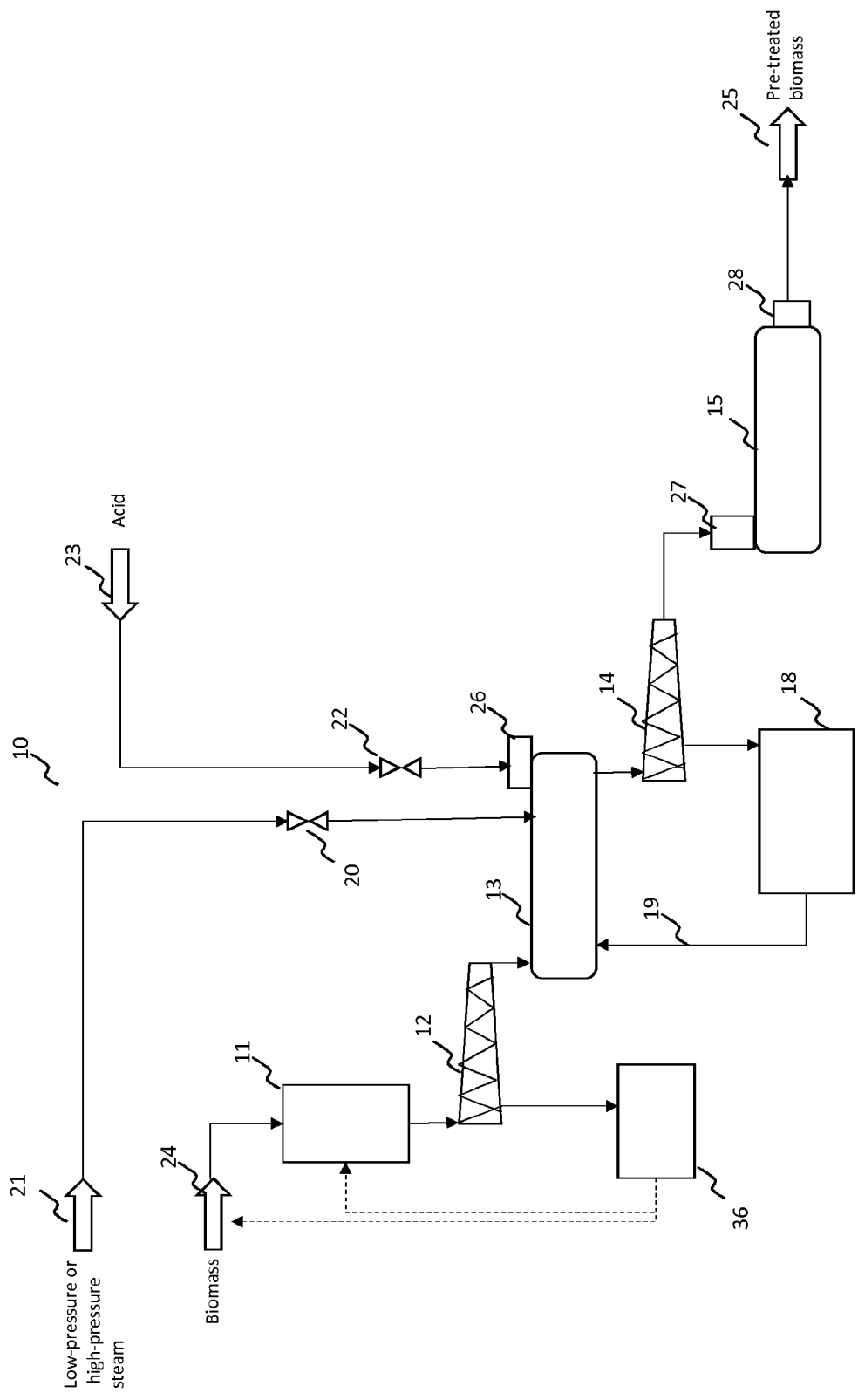
FIG. 1 is a schematic view of an embodiment of the system according to the present invention.

In the drawings, similar or corresponding elements are denoted by the same reference numbers.

For the purpose of this disclosure, the term longitudinal refers to the direction along which a body, part or element has its greatest extension. Further, when the term longitudinal is used in connection with the axes of screws, the longitudinal axis corresponds to the rotational axis of the screw.

Turning first to FIG. 1, where a system according to an embodiment of the present invention is shown. FIG. 1 is a schematic block diagram of a system 10 for biomass treatment according to an embodiment of the present invention. The lignocellulosic biomass 24 may be treated in different processes, such as a soaking process, before feeding the biomass material to the storage vessel, bin or silo 11. The biomass material may be, for example, wood chips of softwood or hardwood, sawdust, grasses, straw, bagasse, kenaf, or other forms of agricultural waste or a combination thereof.

The lignocellulosic biomass 24, for example, wet biomass may have a moisture content in the range of 5-80%, in embodiments the DM (dry matter/dry material) is about 40-45%, and may have a temperature in a range of about 20-40° C.

The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12.

Figure 2:
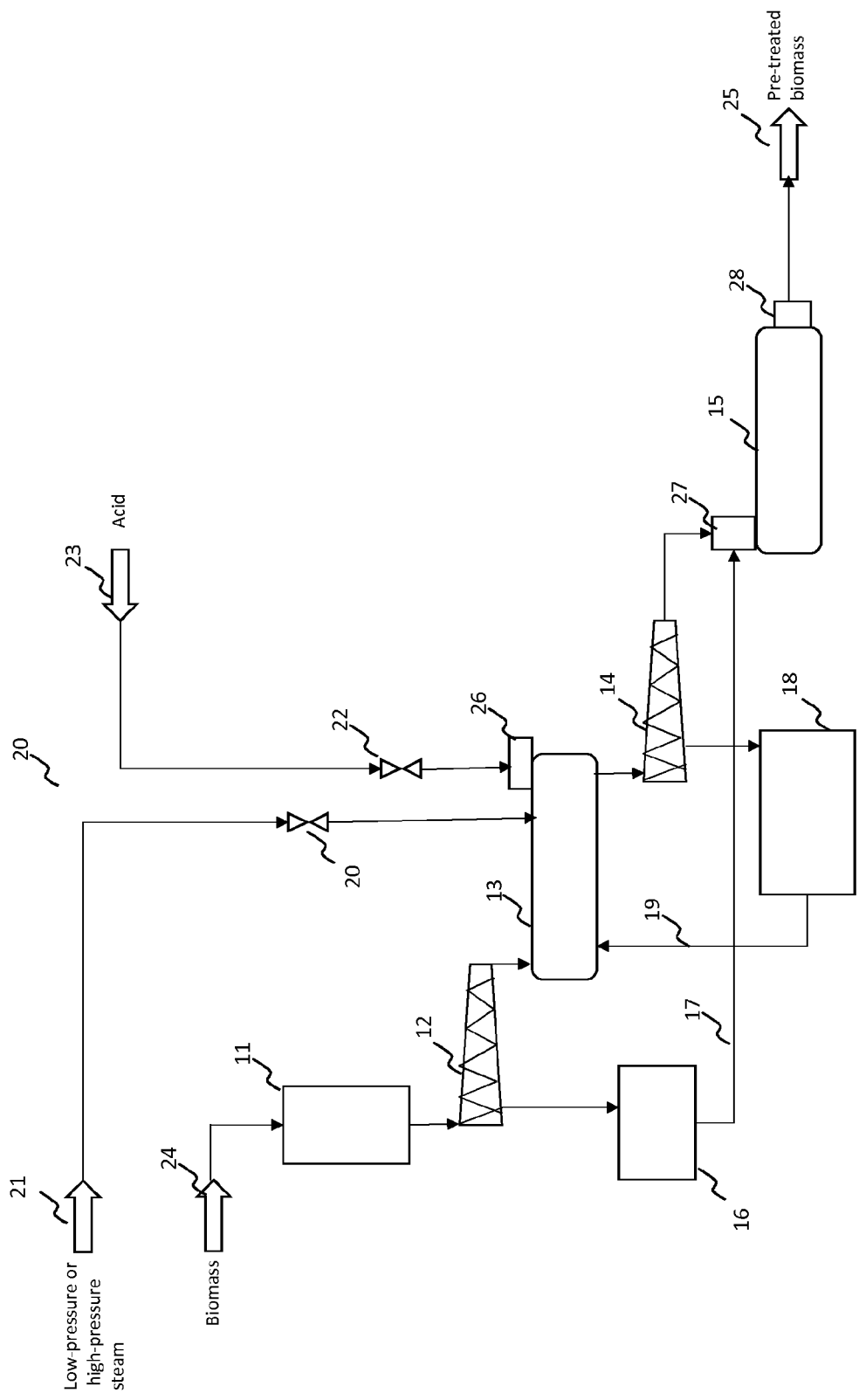
FIG. 2 is a schematic view of another embodiment of the system according to the present invention.

The filtrate from the de-watering stage 12 is led to a water treatment stage 36, which in some embodiments may include, for example, a collector unit or filtrate tank 16 and a filtrate feeding arrangement 17 arranged to feed filtrate from the filtrate tank 16 to a reactor stage 15, see e.g. FIG. 2. The water treatment stage may also be a water-purifying unit, which can be, for example, a biological purifying unit or a chemical purifying unit, or a unit for changing pH of the water by adding an acid or a base. In some embodiments, the collector unit or filtrate tank include a water-purifying unit, which can be, for example, a biological purifying unit or a chemical purifying unit, or a unit for changing pH of the water by adding an acid or a base.

The treated liquid, e.g. the purified water, may be circulated into the process at different stages, as shown in FIG. 1. Further, the treated liquid can be used in the process as described below with reference to, for example, FIG. 2-9. A screening stage may be arranged up-stream the water treatment stage 36 in order to collect any solids that has passed through the de-watering screens together with the filtrate. The solids may then be re-circulated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw, or a P REX-impregnation system (a Valmet product). A DM may be about 25-45% or, preferably, about 30-35% after the addition stage 13.

A second de-watering stage 14 may be provided down-stream the addition stage 13 and up-stream the reactor stage 15. The reactor stage 15 and the addition stage 13 may be operatively coupled to the second de-watering stage 14. The biomass material has preferably about 45-70% DM, or preferably about 50-60%, after the second de-watering stage 14. The filtrate may be led to a filtrate tank 18 for use in the process. A screening stage may be arranged up-stream the filtrate tank 18 in order to collect any solids that has passed through the de-watering screens together with the filtrate, as described below, for example, in connection with FIG. 6. The collected filtrate may be fed back into the loop in the addition stage 13 via a re-circulation arrangement 19.

Turning now to FIG. 2, where a system according to an embodiment of the present invention is shown. FIG. 2 is a schematic block diagram of a system 20 for biomass treatment according to an embodiment of the present invention. The lignocellulosic biomass 24 may be treated in different processes, such as a soaking process, before feeding the biomass material to the storage vessel, bin or silo 11. The biomass material may be, for example, wood chips of softwood or hardwood, sawdust, grasses, straw, bagasse, kenaf, or other forms of agricultural waste or a combination thereof.

The lignocellulosic biomass 24, for example, wet biomass may have a moisture content in the range of 5-80%, in embodiments the DM (dry matter/dry material) is about 40-45%, and may have a temperature in a range of about 20-40° C.

The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12.

The filtrate from the de-watering stage 12 is led to a collector unit or filtrate tank 16 for use in the process. A screening stage may be arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw or a PREX-impregnation system (a Valmet product). A DM may be about 25-45% or, preferably, about 30-35% after the addition stage 13.

A filtrate feeding arrangement 17 is arranged to feed filtrate from the filtrate tank 16 to a reactor stage 15, e.g. a pre-hydrolysis reactor 15, to e.g. an inlet 27 of the reactor stage 15.

A second de-watering stage 14 may be provided downstream the addition stage 13 and up-stream the reactor stage 15. The reactor stage 15 and the addition stage 13 may be operatively coupled to the second de-watering stage 14. The biomass material has preferably about 45-70% DM, or preferably about 50-60%, after the second de-watering stage 14. The filtrate may be led to a filtrate tank 18 for use in the process. A screening stage may be arranged up-stream the filtrate tank 18 in order to collect any solids that has passed through the de-watering screens together with the filtrate, as described below in connection with FIG. 5. The collected filtrate may be fed back into the loop in the addition stage 13 via a re-circulation arrangement 19.

Figure 3:
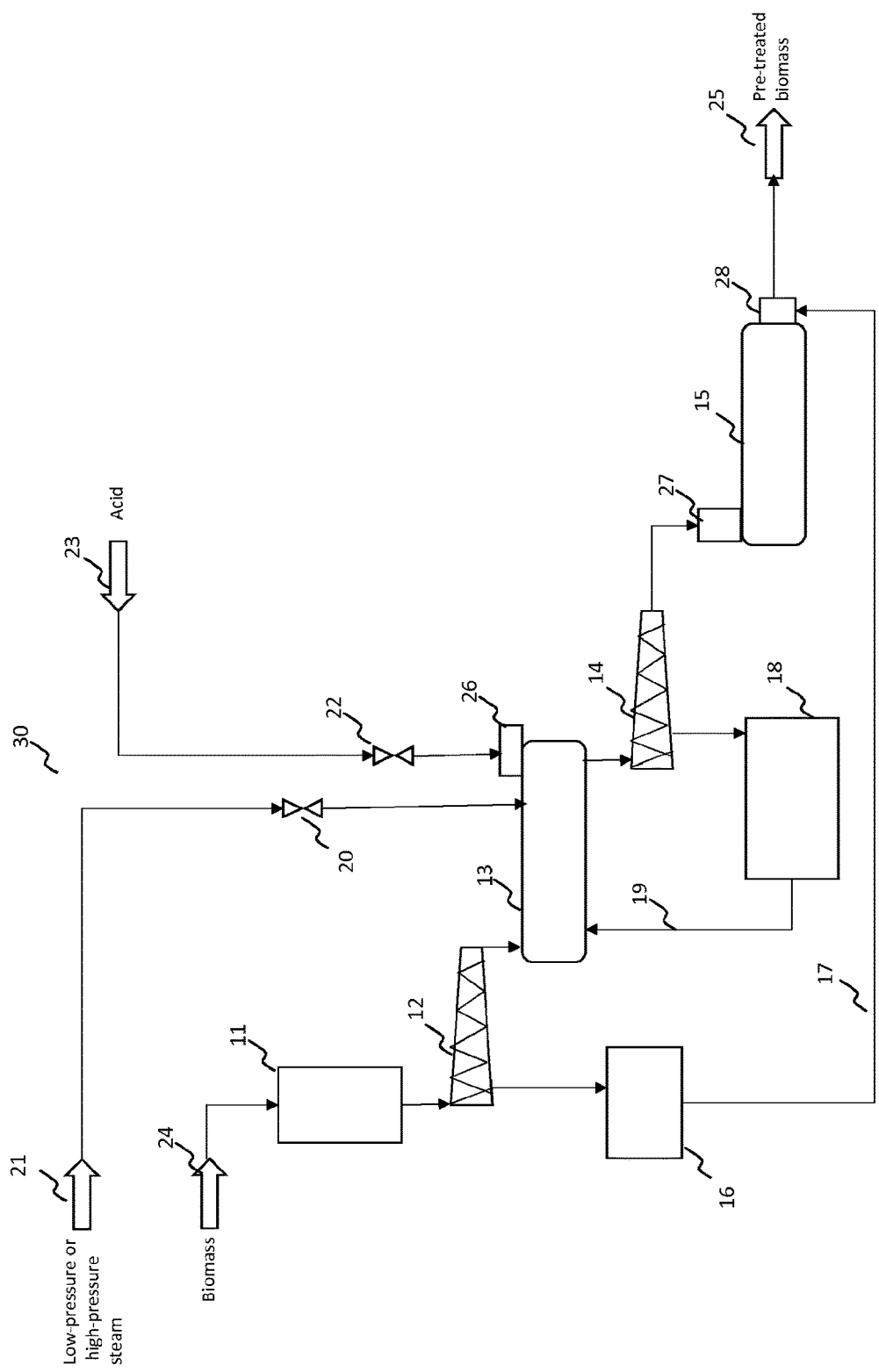
FIG. 3 is a schematic view of yet another further embodiment of the system according to the present invention.

With reference now to FIG. 3, a further embodiment of the present invention will be described. The system 30 includes a storage unit, e.g. a silo, 11 to which the lignocellulosic biomass 24, for example, wet biomass having a moisture content in the range of 5-80%, in embodiments the DM (dry matter/dry material) is about 40-45%, and a temperature in a range of about 20-40° C. is provided.

Thereafter, the biomass material is fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage may be arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw or a PREX-impregnation system (a Valmet product). A DM may be about 25-45% or, preferably, about 30-35% after the addition stage 13.

A filtrate feeding arrangement 17 is arranged to feed filtrate from the filtrate tank 16 to a reactor stage 15, e.g. a pre-hydrolysis reactor 15. In this embodiment, the filtrate is fed to a discharge part 28 of the reactor stage 15, e.g. to clean a discharge screw is there one arranged in the reactor 15, or to clean the discharge part 28 and/or to dilute the discharged treated biomass.

A second de-watering stage 14 may be provided downstream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A screening stage 37, shown in FIG. 6, may be arranged up-stream the filtrate tank 18 in order to collect any solids that has passed through the de-watering screens together with the filtrate, as described below in connection with FIG. 6. The collected filtrate may be fed back into the loop in the addition stage 13 via a re-circulation arrangement 19.

Figure 4:
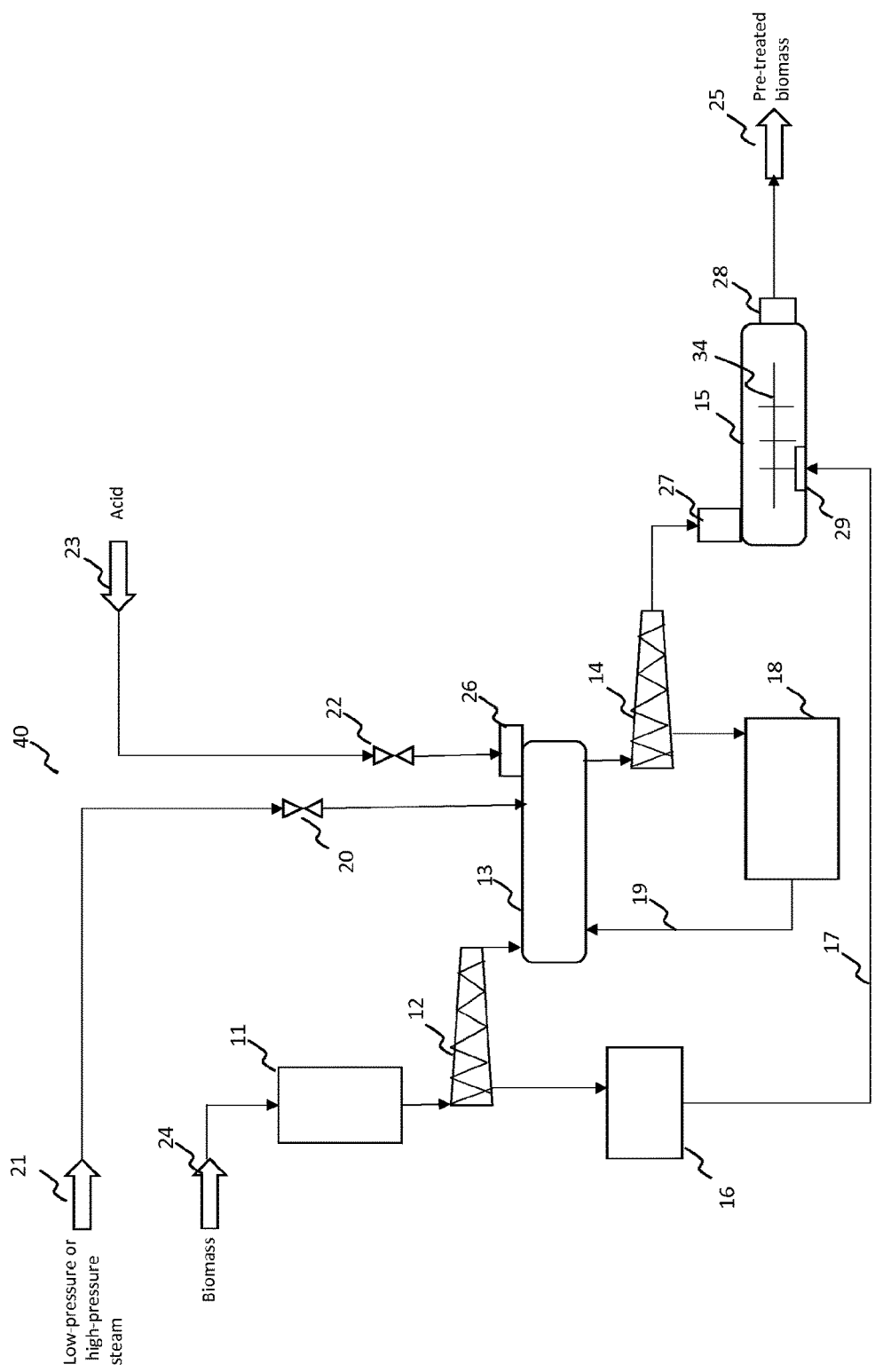
FIG. 4 is a schematic view of an embodiment of the system according to the present invention.

Turning now to FIG. 4, yet another embodiment of the present invention will be described. The system 40 includes a storage unit, e.g. a silo, 11 to which the lignocellulosic biomass 24, for example, wet biomass having a moisture content in the range of 5-80%, in embodiments the DM (dry matter/dry material) is about 40-45%, and a temperature in a range of about 20-40° C. is provided.

The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage may be arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw, or a PREX-impregnation system (a Valmet product). A DM may be about 25-45% or, preferably, about 30-35% after the addition stage 13.

A filtrate feeding arrangement 17 is arranged to feed filtrate from the filtrate tank 16 to a reactor stage 15, e.g. a pre-hydrolysis reactor 15. In this embodiment, the filtrate is fed to cleaning nozzles 29 of the reactor stage to clean a reactor screw 34.

A second de-watering stage 14 may be provided downstream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A screening stage may be arranged up-stream the filtrate tank 18 in order to collect any solids that has passed through the de-watering screens together with the filtrate, as described below in connection with FIG. 5. The collected filtrate may be fed back into the loop in the addition stage 13 via a re-circulation arrangement 19.

Figure 5:
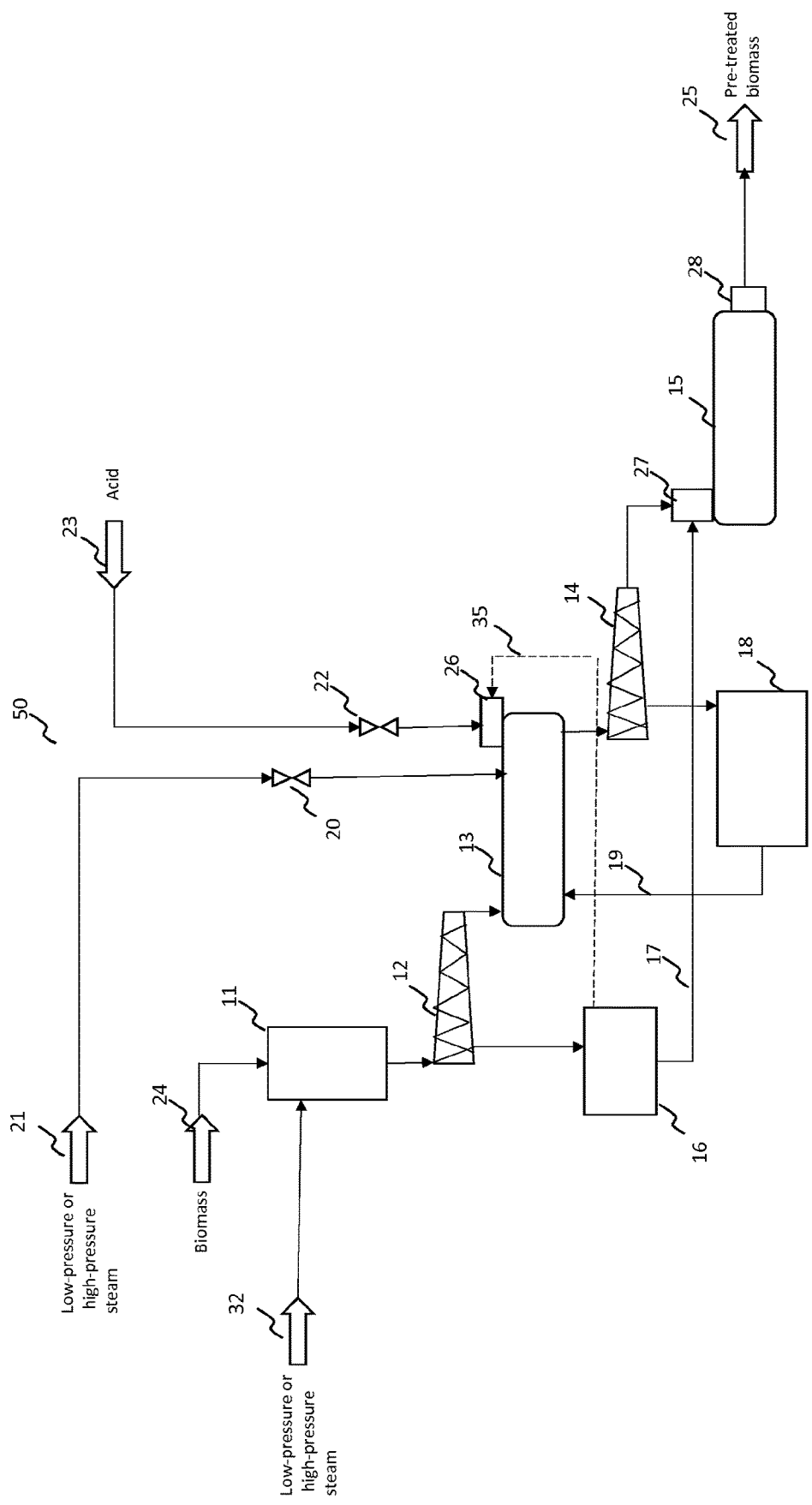
FIG. 5 is a schematic view of a further embodiment of the system according to the present invention.

With reference now to FIG. 5, another embodiment of a system according to the present invention will be described.

The system 50 includes a storage unit, e.g. a silo, 11 to which the lignocellulosic biomass 24, for example, wet biomass having a moisture content in the range of 5-80%, in embodiments the DM (dry matter/dry material) is about 40-45%, and a temperature in a range of about 20-40° C. is provided. The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage may be arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw, or a PREX-impregnation system (a Valmet product). A DM may be about 25-45% or, preferably, about 30-35% after the addition stage 13.

A filtrate feeding arrangement 17 is arranged to feed filtrate from the filtrate tank 16 to a reactor stage 15, e.g. a pre-hydrolysis reactor 15. In this embodiment, the filtrate is fed to the reactor stage, e.g. an inlet 27 of the reactor stage 15, e.g. to be sprayed over the incoming biomass material, and via a second filtrate feeding arrangement 35 to the acid spraying system 26 if more liquid is need to maintain a balance in the added liquid.

A second de-watering stage 14 may be provided down-stream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A screening stage may be arranged up-stream the filtrate tank 18 in order to collect any solids that has passed through the de-watering screens together with the filtrate, as described below in connection with FIG. 6. The collected filtrate may be fed back into the loop in the addition stage 13 via a re-circulation arrangement 19.

Figure 6:
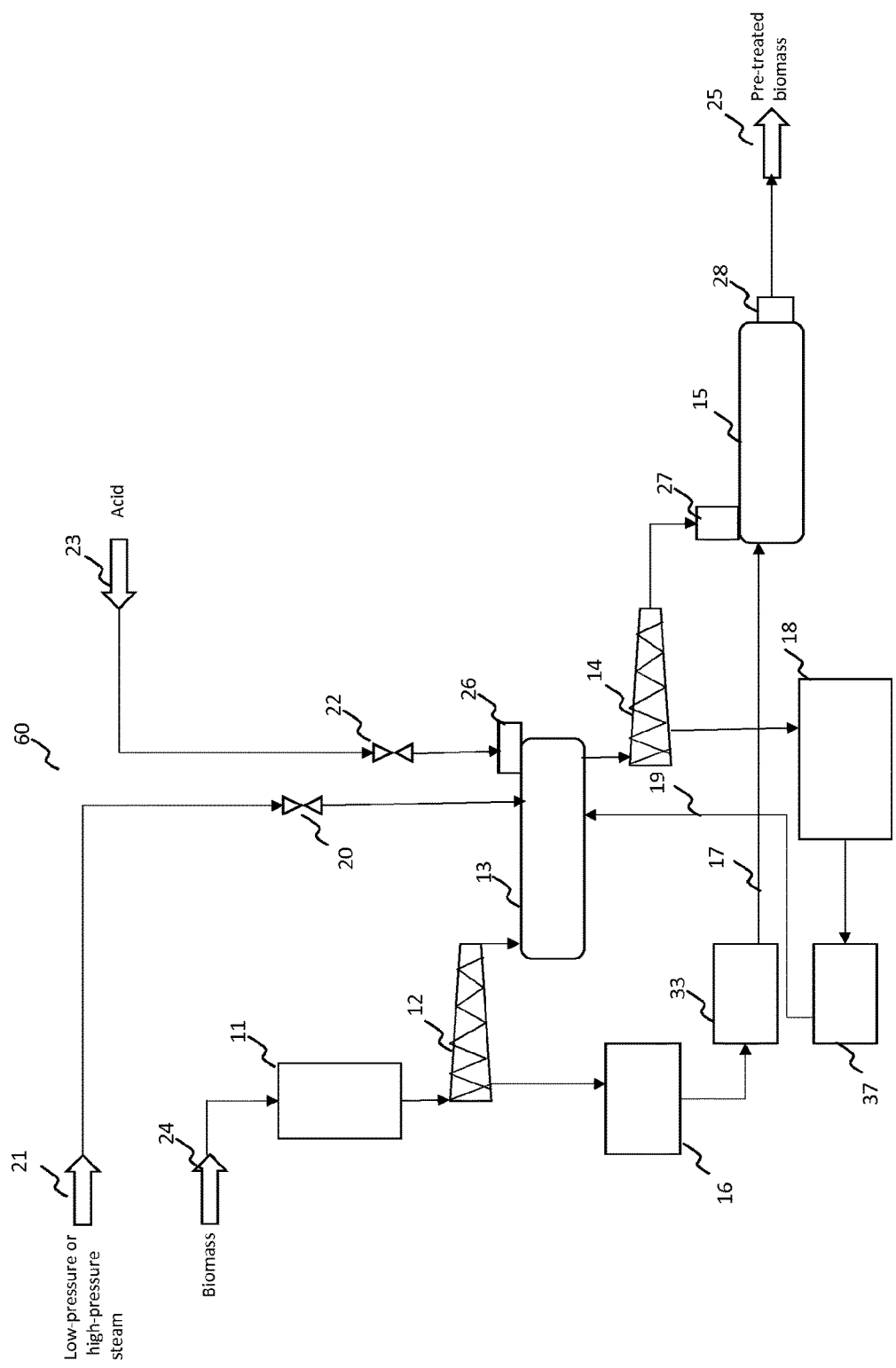
FIG. 6 is a schematic view of yet another embodiment of the system according to the present invention.

With reference now to FIG. 6, a further embodiment of the system according to the present invention will be described.

The system 60 includes a storage unit, e.g. a silo, 11 to which the lignocellulosic biomass 24, for example, wet biomass having a moisture content in the range of 5-80%, in embodiments the DM (dry matter/dry material) is about 40-45%, and a temperature in a range of about 20-40° C. is provided. The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage may be arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

A recovery and refining stage or screening stage 33 is coupled to the filtrate tank 16 to screen the filtrate to for example remove any solids present in the filtrate. The solids may then be recirculated to the biomass material 24 provided into the process. Thereafter, the refined filtrate may be fed to the reactor stage 15 via the filtrate feeding arrangement 17, for example, as described with reference to FIG. 1-4.

A second de-watering stage 14 may be provided down-stream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A recovery and refining or screening stage 37 is arranged up-stream the filtrate tank 18 in order to collect any solids that has passed through the de-watering screens together with the filtrate. Thereafter, the collected filtrate may be fed back into the loop in the addition stage 13 via a re-circulation arrangement 19.

Figure 7:
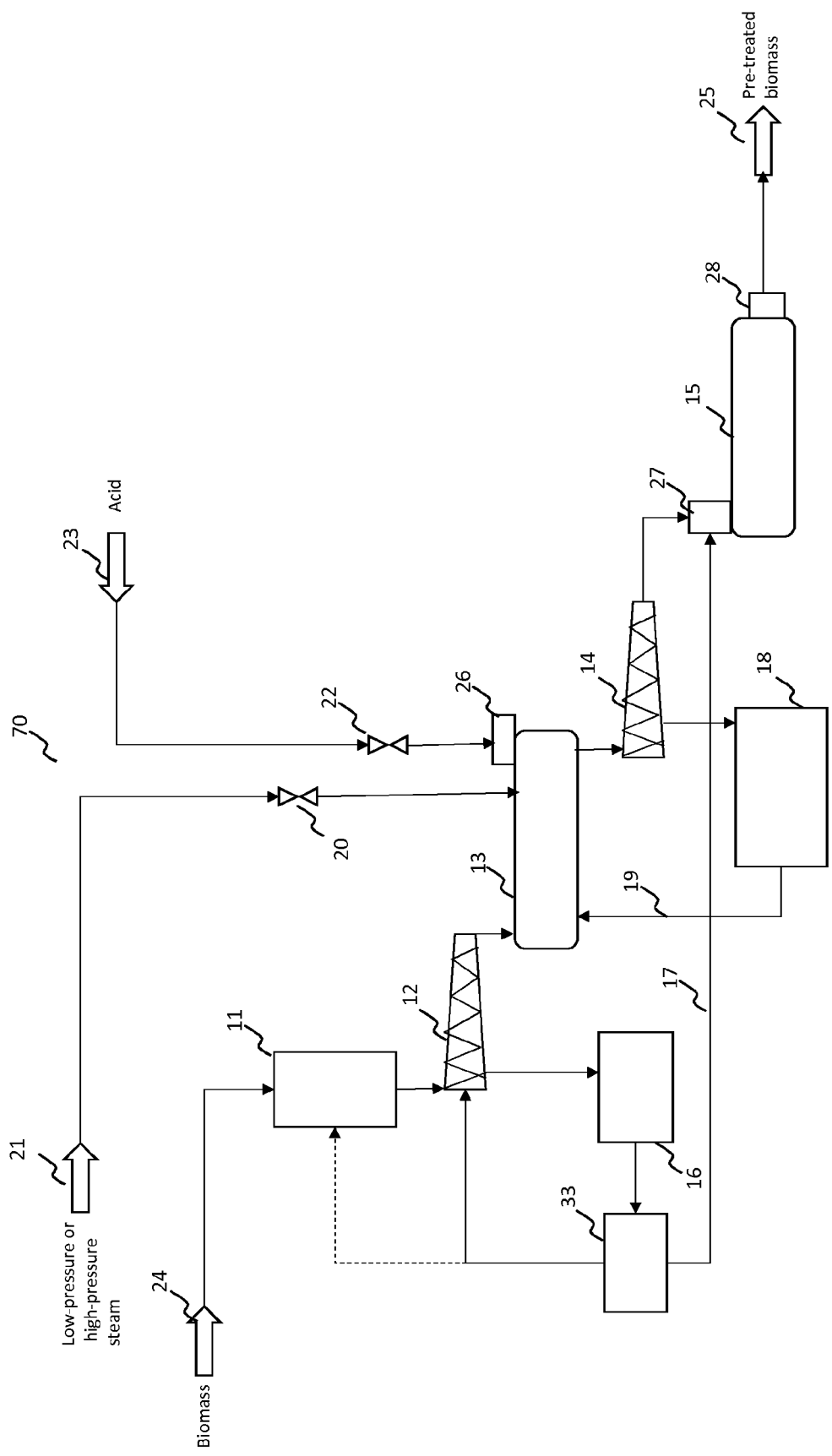
FIG. 7 is a schematic view of a further embodiment of the system according to the present invention.
Figure 8:
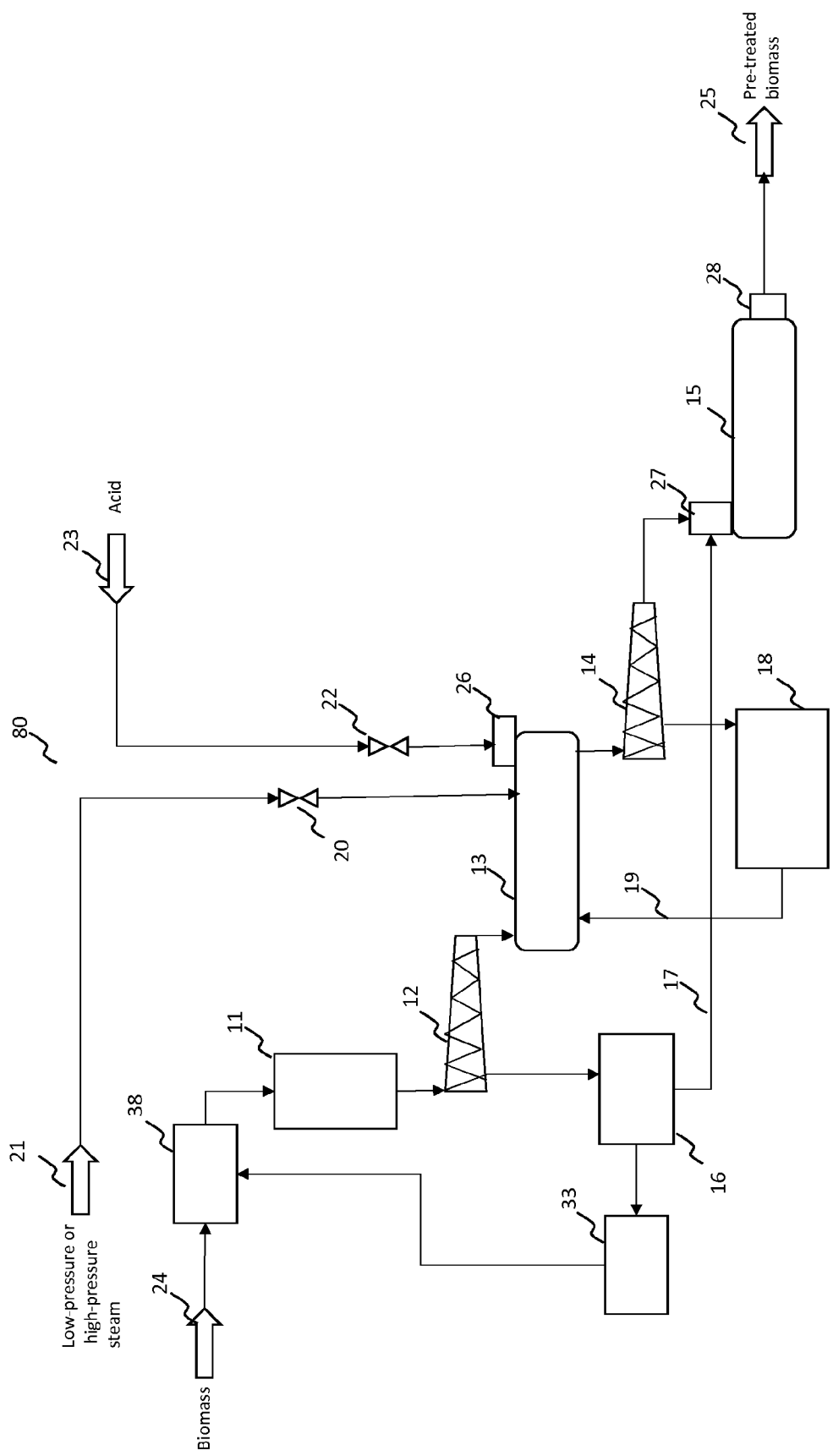
FIG. 8 is a schematic view of an embodiment of the system according to the present invention.

With reference to FIG. 7, yet another embodiment of the system according to the present invention will be described. The system 70 includes a storage unit, e.g. a silo, 11 to which the lignocellulosic biomass 24, for example, wet biomass, e.g. wood chips, having a moisture content in the range of 5-80%, in embodiments the DM (dry matter/dry material) is about 40-45%, and a temperature in a range of about 20-40° C. is provided. The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage 33 is arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

Hence, a recovery and refining stage or screening stage 33 is coupled to the filtrate tank 16 to screen the filtrate to for example remove any solids present in the filtrate. The solids may then be recirculated to the biomass material 24 provided into the process. Thereafter, the refined filtrate is be fed to the reactor stage 15 via the filtrate feeding arrangement 17, for example, as described with reference to FIG. 2-5. In embodiments of the present invention, a main part of the refined filtrate is fed to the reactor stage 15 and a fraction of the filtrate, for example, 1-5% is fed upstream in the process, for example, to the storage vessel or silo 11 as shown in FIG. 7 and/or to a raw material washer 38, or biomass washer, or wood chip washer as in the system 80 shown in FIG. 8.

A second de-watering stage 14 may be provided downstream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A recovery and refining or screening stage 33 is arranged up-stream the filtrate tank 18 in order to collect any solids that has passed through the de-watering screens together with the filtrate. Thereafter, the collected filtrate may be fed back into the loop in the addition stage 13 via a re-circulation arrangement 19.

Figure 9:
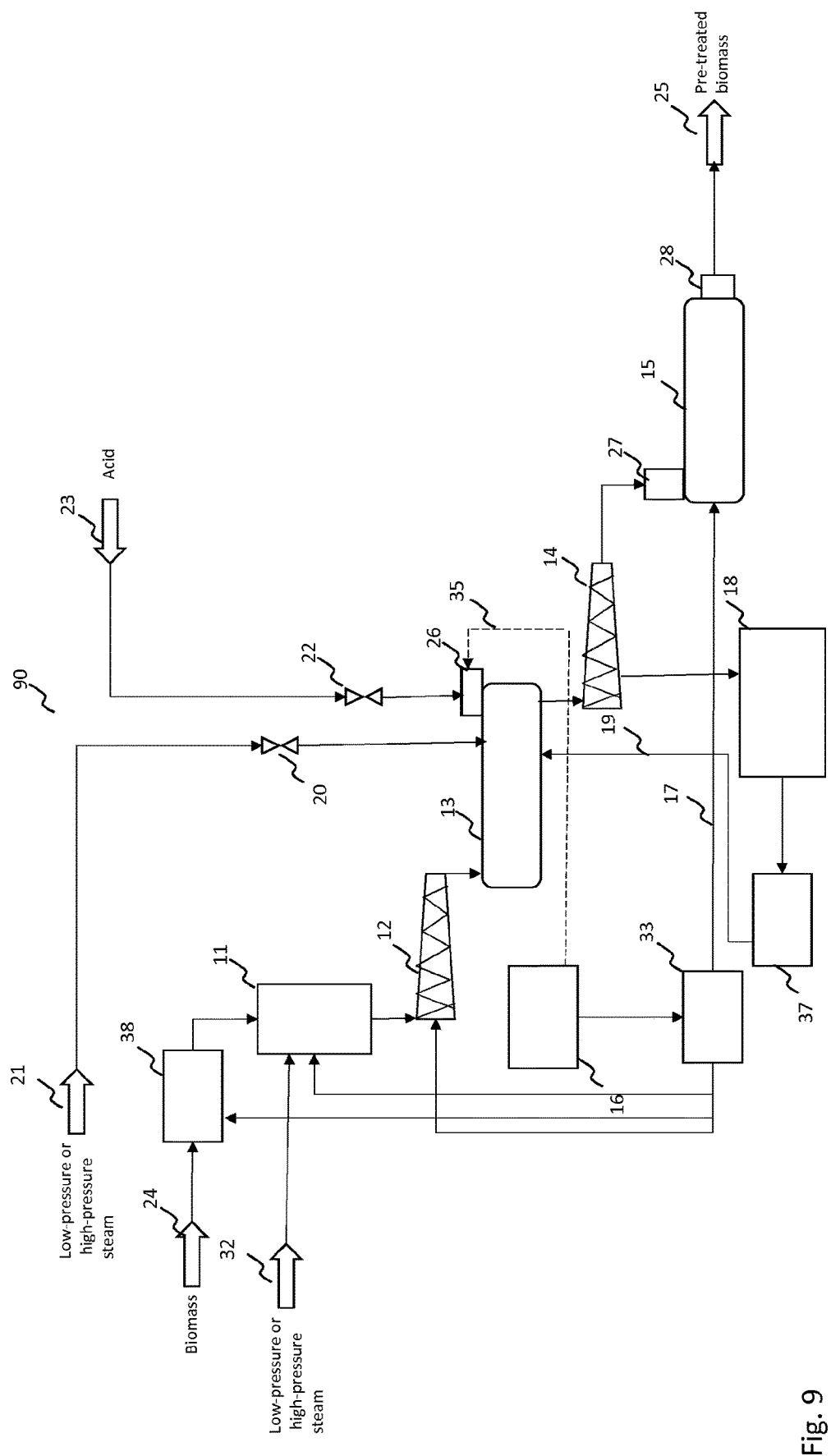
FIG. 9 is a schematic view of a further embodiment of the system according to the present invention.

With reference to FIG. 9, yet another embodiment of the system according to the present invention will be described. The system 90 includes a storage unit, e.g. a silo, 11 to which the lignocellulosic biomass 24, for example, wet biomass, e.g. wood chips, having a moisture content in the range of 5-80%, in embodiments the DM (dry matter/dry material) is about 40-45%, and a temperature in a range of about 20-40° C. is provided. The biomass material is thereafter fed further to a first de-watering stage 12, for example a least one feed screw 12, e.g. a plug screw feeder. In embodiments of the present invention, the biomass material has about 45-70% DM, or preferably about 50-60%, after the de-watering stage 12. The filtrate from the de-watering stage 12 is led to a collector unit or filtrate tank 16 for use in the process. A screening stage 33 is arranged up-stream the filtrate tank 16 in order to collect any solids that has passed through the de-watering screens together with the filtrate. The solids may then be recirculated back into the raw material flow, for example, to the storage vessel 11.

The de-watered biomass material is fed further to an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

Hence, a recovery and refining stage or screening stage 33 is coupled to the filtrate tank 16 to screen the filtrate to for example remove any solids present in the filtrate. The solids may then be recirculated to the biomass material 24 provided into the process. Thereafter, the refined filtrate is be fed to the reactor stage 15 via the filtrate feeding arrangement 17, for example, as described with reference to FIG. 2-5. For example, the filtrate may be fed to a discharge part 28 of the reactor stage 15, e.g. to clean a discharge screw is there one arranged in the reactor 15, or to clean the discharge part 28 and/or to dilute the discharged treated biomass, or to cleaning nozzles 29 arranged in the reactor vessel to clean a reactor screw 34, or to an inlet 27 of the reactor stage 15, e.g. to be sprayed over the incoming biomass material, and/or via a second filtrate feeding arrangement 35 to the acid spraying system 26 if more liquid is need to maintain a balance in the added liquid.

In embodiments of the present invention, a main part of the refined filtrate is fed to the reactor stage 15 and a fraction of the filtrate, for example, 1-5% is fed upstream in the process, for example, to the storage vessel or silo 11 and/or to a raw material washer 38, or biomass washer, or wood chip washer.

A second de-watering stage 14 may be provided downstream the addition stage 13 and up-stream the reactor stage 15. The reactor stage 15 and the addition stage 13 may be operatively coupled to the second de-watering stage 14. The biomass material has about 45-70% DM, or preferably about 50-60%, after the second de-watering stage 14. The filtrate may be led to a filtrate tank 18 for use in the process. A recovery and refining or screening stage 33 is arranged up-stream the filtrate tank 18 in order to collect any solids that has passed through the de-watering screens together with the filtrate. Thereafter, the collected filtrate may be fed back into the loop in the addition stage 13 via a re-circulation arrangement 19.

Figure 10:
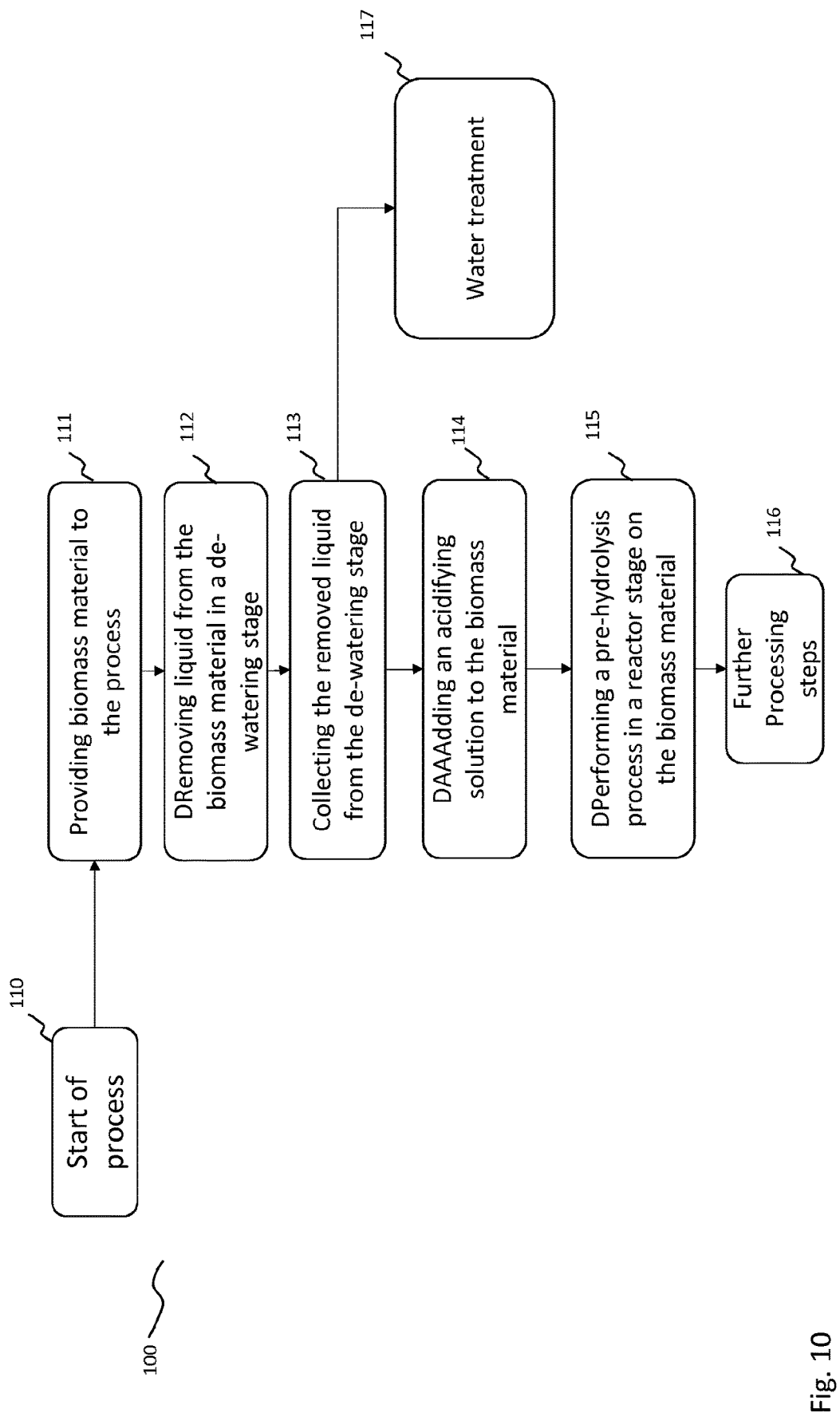
FIG. 10 illustrates steps of a method according to an embodiment of the present invention.

With reference to FIG. 10, a method according to an embodiment of the present invention will be described. The method relates to treatment and feeding of lignocellulosic biomass which is treated at elevated temperature and pressure with steam or mixtures of steam and acidifying solutions. The lignocellulosic biomass material, such as wood chips, may be treated in different processes, such as a soaking process, before feeding the biomass material to a storage vessel, bin or silo 11. The biomass material 24 provided into the process may be, for example, wood chips of softwood or hardwood, sawdust, grasses, straw, bagasse, kenaf, or other forms of agricultural waste or a combination thereof. The lignocellulosic biomass may, for example, be wet biomass may have a moisture content in the range of 5-80%, in embodiments the DM (dry matter/dry material) is about 40-45%, and may have a temperature in a range of about 20-40° C.

In the process 100, the lignocellulosic biomass material 24 is fed, at step 111 to a silo 11. Thereafter, at step 112, liquid is removed from the biomass in a first de-watering stage 12, for example a least one feed screw 12, e.g. a plug screw feeder. In embodiments of the present invention, the biomass material has about 45-70% DM, or preferably about 50-60%, after the de-watering stage 12.

At step 113, the filtrate from the de-watering stage 12 is collected and provided to water treatment 117.

At step 114, an addition step is performed in an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

At step 115, a treatment process in a reactor stage 15 is performed, e.g. a pre-hydrolysis process, on the biomass material.

At step 116, the treated biomass material may be fed to further processing steps.

Figure 11:
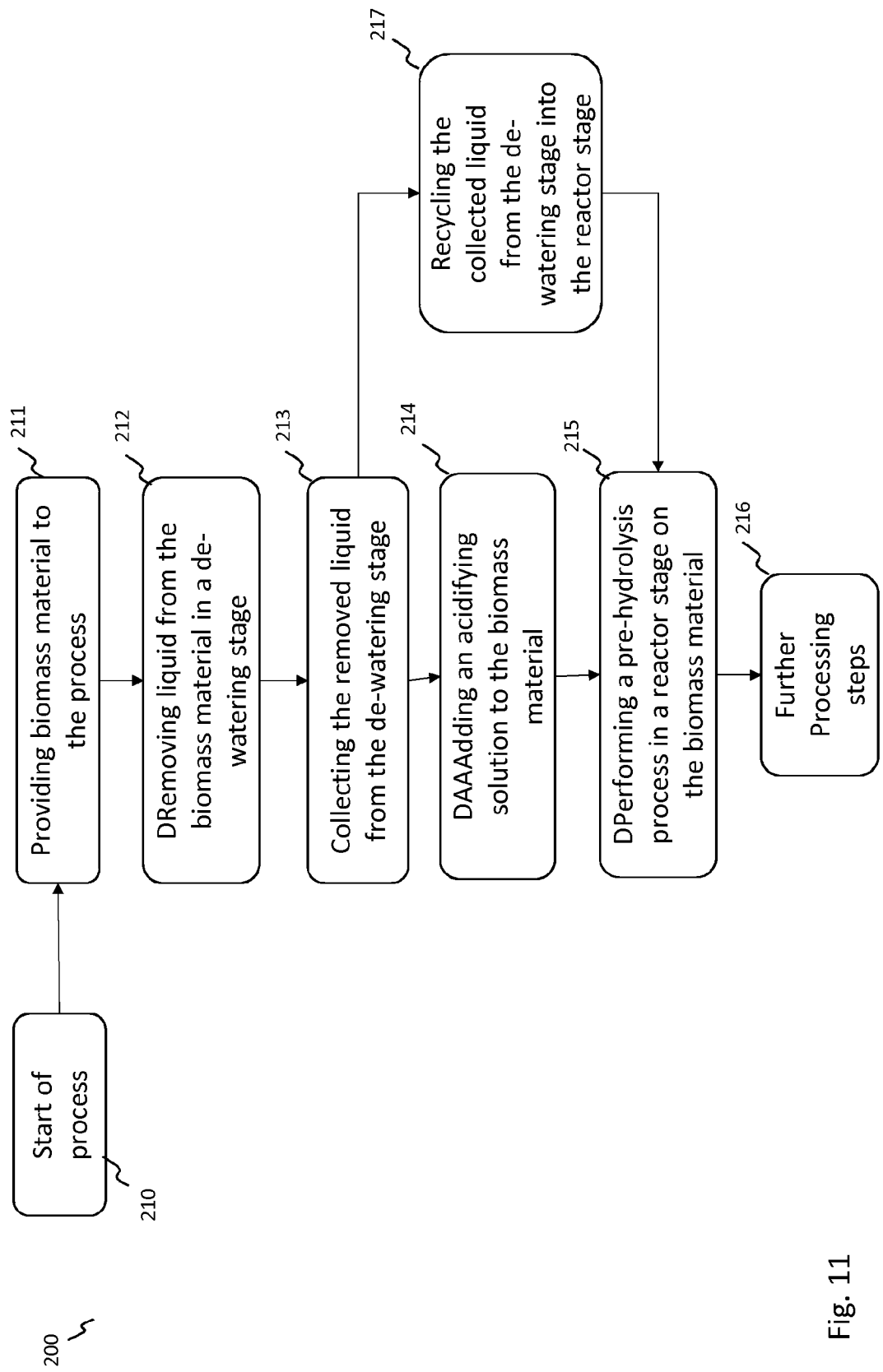
FIG. 11 illustrates steps of a method according a further embodiment of the present invention.

Referring now to FIG. 11, another embodiment of the method according to the present invention will be described. In the process 200, the lignocellulosic biomass material 24 is fed, at step 211 to a silo 11. Thereafter, at step 212, liquid is removed from the biomass in a first de-watering stage 12, for example a least one feed screw 12, e.g. a plug screw feeder. In embodiments of the present invention, the biomass material has about 45-70% DM, or preferably about 50-60%, after the de-watering stage 12.

At step 213, the filtrate from the de-watering stage 12 is collected in a collector unit or filtrate tank 16 for use in the process.

At step 214, an addition step is performed in an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

At step 215, a treatment process in a reactor stage 15 is performed, e.g. a pre-hydrolysis process, on the biomass material.

At step 217, the filtrate collected from the first de-watering stage 12 is re-cycled or fed to the reactor stage 15 using a filtrate feeding arrangement 17 arranged to feed filtrate from the filtrate tank 16 to the reactor stage 15, e.g. a pre-hydrolysis reactor 15. For example, the filtrate may be fed to a discharge part 28 of the reactor stage 15, e.g. to clean a discharge screw is there one arranged in the reactor 15, or to clean the discharge part 28 and/or to dilute the discharged treated biomass, or to cleaning nozzles 29 arranged in the reactor vessel to clean a reactor screw 34, or to an inlet 27 of the reactor stage 15, e.g. to be sprayed over the incoming biomass material, and/or via a second filtrate feeding arrangement 35 to the acid spraying system 26 if more liquid is need to maintain a balance in the added liquid.

At step 216, the treated biomass material may be fed to further processing steps.

Figure 12:
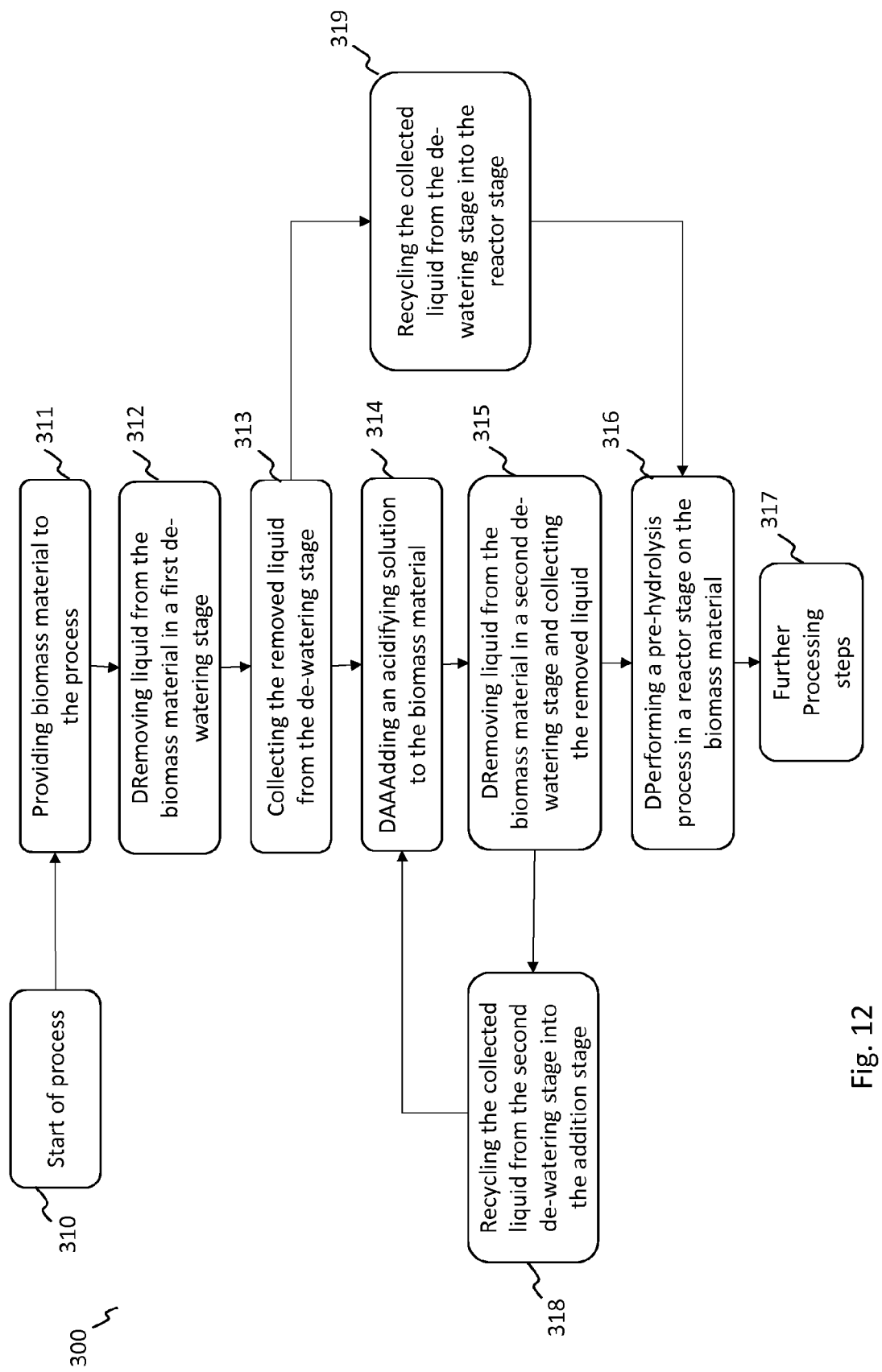
FIG. 12 illustrates steps of a method according to an embodiment of the present invention.

With reference to FIG. 12, yet another method according to the present invention will be described. The method relates to treatment and feeding of lignocellulosic biomass which is treated at elevated temperature and pressure with steam or mixtures of steam and acidifying solutions. The lignocellulosic biomass material may be treated in different processes, such as a soaking process, before feeding the biomass material to a storage vessel, bin or silo 11. The biomass material 24 provided into the process may be, for example, wood chips of softwood or hardwood, sawdust, grasses, straw, bagasse, kenaf, or other forms of agricultural waste or a combination thereof. The lignocellulosic biomass may, for example, be wet biomass may have a moisture content in the range of 5-80%, in embodiments the DM (dry matter/dry material) is about 40-45%, and may have a temperature in a range of about 20-40° C.

In the process 300, the lignocellulosic biomass material 24 is fed, at step 311 to a silo 11. Thereafter, at step 312, liquid is removed from the biomass in a first de-watering stage 12, for example a least one feed screw 12, e.g. a plug screw feeder. In embodiments of the present invention, the biomass material has about 45-70% DM, or preferably about 50-60%, after the de-watering stage 12.

At step 313, the filtrate from the de-watering stage 12 is collected in a collector unit or filtrate tank 16 for use in the process.

At step 314, an addition step is performed in an addition stage 13 where chemicals, such as e.g. acidifying chemicals 23, is added via an acid spraying system 26 and/or steam 21, e.g. high pressure steam at a pressure of about 650-4000 kPa or low-pressure steam at a pressure of about 90-1200 kPa, is added via a valve 20. In embodiments of the present invention, the addition stage may comprise an impregnator, a soaking unit or a mixer screw. A DM may be about 25-45% or, preferably, about 30-35% after the addition stage 13.

At step 315, a second de-watering step is performed down-stream the addition stage 13. The biomass material has about 45-70% DM, or preferably about 50-60%, after the second de-watering stage 14. The filtrate may be led to a filtrate tank 18 for use in the process. A screening stage may be arranged up-stream the filtrate tank 18 in order to collect any solids that has passed through the de-watering screens together with the filtrate, as described below in connection with FIG. 5. At step 318, the collected filtrate is recycled into the process loop in the addition stage 13 via a re-circulation arrangement 19.

At step 316, a treatment process in a reactor stage 15 is performed, e.g. a pre-hydrolysis process, on the biomass material.

At step 319, the filtrate collected from the first de-watering stage 12 is re-cycled or fed to the reactor stage 15 using a filtrate feeding arrangement 17 arranged to feed filtrate from the filtrate tank 16 to the reactor stage 15, e.g. a pre-hydrolysis reactor 15. For example, the filtrate may be fed to a discharge part 28 of the reactor stage 15, e.g. to clean a discharge screw is there one arranged in the reactor 15, or to clean the discharge part 28 and/or to dilute the discharged treated biomass, or to cleaning nozzles 29 arranged in the reactor vessel to clean a reactor screw 34, or to an inlet 27 of the reactor stage 15, e.g. to be sprayed over the incoming biomass material, and/or via a second filtrate feeding arrangement 35 to the acid spraying system 26 if more liquid is need to maintain a balance in the added liquid.

At step 317, the treated biomass material may be fed to further processing steps.

From the foregoing, it will be appreciated that specific embodiments of the disclosure have been described herein with purposes of illustration, but that various modifications may be made without deviating from the spirit and scope of the invention. Accordingly, the invention shall not be considered limited to the embodiments illustrated, but can be modified and altered in many ways by one skilled in the art, without departing from the scope of the appended claims.

The invention claimed is:

1. A system for treating biomass material, comprising:
a first dewatering stage configured to receive biomass material, to remove liquid from the biomass material, and to feed the biomass material forward in the system;
a first filtrate tank configured to receive and collect the liquid removed in the first dewatering stage;
an addition stage located downstream of the dewatering stage and operatively coupled to the first dewatering stage, the addition stage configured to receive the dewatered biomass material, wherein the addition stage comprises inlets for adding an acid-containing solution into the addition stage, to treat the biomass;
a reactor stage configured to receive the biomass material treated in the addition stage and to perform a pre-hydrolysis process to the biomass material; and
a filtrate feeder configured to feed the liquid from the first filtrate tank to the reactor stage,
wherein the first dewatering stage and the reactor stage are configured to allow the liquid collected from the first dewatering stage to recycle to the reactor stage.

2. The system of claim 1, wherein the filtrate feeder is configured to provide the liquid from the first filtrate tank to cleaning nozzles of the reactor stage.

3. The system of claim 1, wherein the filtrate feeder is configured to provide the liquid from the first filtrate tank to a discharge unit of the reactor stage.

4. The system of claim 1, wherein the filtrate feeder is configured to provide the liquid from the first filtrate tank to an inlet part of the reactor stage.

5. The system of claim 1, wherein the addition stage comprises an impregnator, a soaking unit, or a mixer screw.

6. The system of claim 1, further comprising a second dewatering stage located downstream of the addition stage and operatively coupled to the addition stage, the second dewatering stage configured to receive biomass material, to remove liquid from the biomass material, and to feed the biomass material forward in the process.

7. The system of claim 1, further comprising:
a second filtrate tank configured to collect removed liquid from the second dewatering stage; and
a recirculation arrangement configured to feed the liquid from the second filtrate tank to the addition stage.

8. The system of claim 1, wherein the inlets for adding the acid-containing solution are controlled to add the acid-containing solution to the biomass material to have an acid content in a range of 0-10% weight/weight of the biomass material.

9. The system of claim 1, wherein the first and second dewatering stages and addition stage are configured to operate at atmospheric pressure.

10. The system of claim 1, wherein the reactor stage is configured to operate at a pressure in a range of 5-25 bar and/or a temperature in a range of 150° C.-230° C.

11. The system of claim 1, comprising a pre-steaming stage located upstream of the first dewatering stage, the pre-steaming stage configured to perform a pre-steaming process on the biomass material.

12. The system of claim 1, comprising a recovery and refining stage coupled to the first filtrate tank and configured to perform a refining process on the filtrate to recover selected compounds from the filtrate.

13. The system of claim 6, comprising a recovery and refining stage coupled to the first filtrate tank and configured to perform a refining process on the filtrate to recover selected compounds from the filtrate.

14. A treatment process for biomass material comprising the steps of:
in a first dewatering stage, receiving the biomass material and removing liquid from the biomass material;
in a first filtrate tank, collecting the removed liquid from the first dewatering stage;
in an addition stage operatively coupled to the first dewatering stage, receiving the dewatered biomass material and adding an acid-containing solution to the biomass material, the addition stage comprising inlets for adding the acid-containing solution;
in a reactor stage, receiving the biomass material treated in the addition stage and performing a pre-hydrolysis process on the biomass material; and
using a filtrate feeder, feeding the liquid from the first filtrate tank to the reactor stage, so as to recycle the liquid collected from first dewatering stage to the reactor stage.

15. The treatment process for biomass material of claim 14, wherein the step of feeding the liquid comprise feeding the liquid from the first filtrate tank to cleaning nozzles of the reactor stage.

16. The treatment process of claim 14, wherein the step of feeding the liquid comprise feeding the liquid from the first filtrate tank to a discharge unit of the reactor stage.

17. The treatment process of claim 14, wherein the step of feeding the liquid comprise feeding the liquid from the first filtrate tank to an inlet part of the reactor stage.

18. The treatment process of claim 14, further comprising:
removing liquid from the biomass material in a second dewatering stage;
collecting the removed liquid from the second dewatering stage; and
recycling the collected liquid from the second dewatering stage to the addition stage.

19. The treatment process of claim 14, further comprising controlling the addition of the acid-containing solution to the biomass material to have an acid content in a range of 0-10% weight/weight of the biomass material.

20. The treatment process of claim 14, further comprising operating the first and second dewatering stages and addition stage at atmospheric pressure.

21. The treatment process of claim 14, further comprising operating the reactor stage at a pressure in a range of 5-25 bar and/or at a temperature in a range of 150° C.-230° C.

22. The treatment process of claim 14, further comprising performing pre-steaming up-stream the first dewatering stage.

23. The treatment process of claim 14, further comprising performing a refining process on the filtrate to recover selected compounds from the filtrate.

24. The treatment process of claim 14, further comprising performing a refining process on the filtrate to recover selected compounds from the filtrate.

* * * * *